United States Patent
Tsuji et al.

(10) Patent No.: US 7,867,370 B2
(45) Date of Patent: Jan. 11, 2011

(54) GAS SENSOR ELEMENT

(75) Inventors: Nobuyuki Tsuji, Okazaki (JP); Akio Tanaka, Gifu (JP); Keigo Mizutani, Okazaki (JP)

(73) Assignee: Denso Corporation, Kariya, Aichi-Pref. (JP)

( * ) Notice: Subject to any disclaimer, the term of this patent is extended or adjusted under 35 U.S.C. 154(b) by 463 days.

(21) Appl. No.: 11/633,434

(22) Filed: Dec. 5, 2006

(65) Prior Publication Data

US 2007/0144905 A1    Jun. 28, 2007

(30) Foreign Application Priority Data

Dec. 28, 2005 (JP) ............................. 2005-378269
Jun. 12, 2006 (JP) ............................. 2006-162345

(51) Int. Cl.
*G01N 7/00* (2006.01)

(52) U.S. Cl. ..................... 204/429; 204/424; 204/428; 204/432; 205/783.5; 205/784.5; 205/785; 73/23.31

(58) Field of Classification Search ......... 204/424–429, 204/431, 432, 406; 205/784, 783.5–785, 205/781; 73/23.31, 23.35
See application file for complete search history.

(56) References Cited

U.S. PATENT DOCUMENTS

| 4,077,775 A | 3/1978 | Lacroix et al. |
| 5,593,558 A * | 1/1997 | Sugino et al. ............... 204/429 |
| 6,129,898 A * | 10/2000 | Watkins et al. ........... 423/239.1 |
| 6,205,843 B1 * | 3/2001 | Tanaka et al. ............... 73/31.06 |
| 6,210,552 B1 | 4/2001 | Mizutani et al. |
| 6,660,145 B2 | 12/2003 | Hotta et al. |
| 6,823,662 B1 * | 11/2004 | Yamamoto et al. ............ 60/286 |
| 2002/0008025 A1 * | 1/2002 | Fujii et al. ................... 204/429 |
| 2003/0146093 A1 * | 8/2003 | Akiyama et al. ............. 204/424 |
| 2003/0154764 A1 | 8/2003 | Stahl et al. |

FOREIGN PATENT DOCUMENTS

| JP | 52-69694 | 6/1976 |
| JP | 54-134697 | 10/1979 |
| JP | 63-066448 | 3/1988 |
| JP | 11-160273 | 6/1999 |
| JP | 2002-181769 | 6/2002 |
| JP | 2003/528314 | 9/2003 |

* cited by examiner

*Primary Examiner*—Nam X Nguyen
*Assistant Examiner*—Susan Thai
(74) *Attorney, Agent, or Firm*—Nixon & Vanderhye P.C.

(57) ABSTRACT

A gas sensor element has a solid electrolyte body of oxygen ionic conductivity, a target gas electrode and a reference gas electrode formed on both surfaces of the solid electrolyte body, respectively, a porous diffusion resistance layer, and a catalyst support trap layer. The porous diffusion resistance layer covers the target gas electrode and through which target gases to be measured are passing. The catalyst support trap layer is formed on the outer surface of the porous diffusion resistance layer and supports noble metal catalyst. In the gas sensor element, the noble metal catalyst is made of platinum, rhodium, palladium supported in the catalyst support trap layer. In particular, an addition amount of palladium in the total amount of the noble metal catalyst is within a range of 2 to 65 wt %.

3 Claims, 10 Drawing Sheets

GAS SENSOR ELEMENT

CROSS-REFERENCE TO RELATED APPLICATIONS

This application is related to and claims priority from Japanese Patent Applications No. 2005-378269 filed on Dec. 28, 2005, and No. 2006-162345 filed on Jun. 12, 2006, the contents of which are hereby incorporated by reference.

BACKGROUND OF THE INVENTION

1. Field of the Invention

The present invention relates generally to a gas sensor element to be employed in a combustion control for an internal combustion engine mounted on automotive vehicles.

2. Description of the Related Art

Considering from a viewpoint of earth environmental protection, alternative fuel engine technologies have been studied and examined, such as direct injection gasoline engines and compresses natural gas (CNG) engines. Following this, gas sensor elements for use in such direct injection gasoline engines and CNG engines have also been attracted interest recently.

However, in the technological field of the direct injection gasoline engine, because the direct injection gasoline engine is different in combustion mechanism from other types of gasoline engines, the direct injection gasoline engine often generates an unburned fuel gas, and emits an exhaust gas including the unburned fuel gas when the direct injection gasoline engine starts and during the operation of the direct injection gasoline engine. Further, the CNG engines have a tendency to increase the amount of hydrogen gas involved in the exhaust gas by a different fuel specification when compared with a case of a conventional gasoline engine. Accordingly, there becomes a problem of causing an output shift of a gas sensor element from a correct output value.

It is considered that such a problem is generated by the difference in the passage speed between hydrogen gas and another combustion gas that are passing through a porous diffusion resistance layer. The porous diffusion resistance layer is capable of limiting the introduction or passage amount of target gases to be measured. That is, because hydrogen gas has a smaller molecular weight than that of another combustion gas such as oxygen gas in air, the hydrogen gas can arrive at or reach a target gas electrode in the gas sensor element faster than another combustion gas. This causes the concentration of hydrogen gas to be increased in the target gases around the target gas electrode. In other words, an excess amount of hydrogen gas becomes present around the target gas electrode. This would cause such an output shift of the gas sensor element from its correct output value.

In particular, an air-fuel sensor (A/F sensor) capable of detecting an air-fuel ratio by using a critical current has a tendency to cause a remarkable output shift from a correct output value thereof. That is, because the A/F sensor has a long diffusion length in the porous diffusion resistance layer, the difference of a diffusion rate between hydrogen gas and another combustion gas becomes large. As a result, such an A/F sensor has a large shift output from a correct output value.

There is a tendency to generate more hydrogen gas in unstable combustion conditions, for example, at the engine start. Thus, there becomes an important problem regarding the output shift of the gas sensor element from a correct output value. In addition, it is necessary as an important matter that an air-fuel ratio (A/F ratio) in an internal combustion engine is shifted to a specified ratio of an optimum combustion condition in order to obtain a superior purifying function as quickly as possible, simultaneously with the temperature rise of a catalyst converter (a three-way catalytic converter), mounted on an exhaust gas pipe, capable of purifying exhaust gas emitted from an internal combustion engine of a vehicle. That is, it is very important to activate or operate the gas sensor element and to provide the correct output of the gas sensor element without any output shift from the correct output value, as quickly as possible.

FIG. 8A is a sectional view of a catalyst support trap layer 92 in a gas sensor element 9 according to a related art, through which target gases such as hydrogen gas $H_2$ and oxygen gas $O_2$ to be measured are passing. FIG. 8B is a sectional view of the catalyst support trap layer 92 of the gas sensor element 9 according to the related art, and FIG. 8B shows that the target gases reach the target gas electrode in a measurement room. FIG. 9 is a detailed sectional view showing the catalyst support trap layer 92 in detail that is formed on the outer peripheral surface 920 of a porous diffusion resistance layer 912 in the gas sensor element 9 according to the related art. FIG. 10A shows components that form the catalyst support trap layer 92 in the gas sensor element 9 according to the related art before breaking its endurance capability (or durability). FIG. 10B shows the components that form the catalyst support trap layer 92 in the gas sensor element 9 according to the related art after breaking its endurance capability (or durability).

As shown in FIGS. 8A, 8B, 9, 10A, and 10B, such a related art technique has proposed the gas sensor element 9 having the catalyst support trap layer 92. For example, Japanese patent No. JP 3488818 and Japanese patent laid open publication No. JP 2002-181769 have disclosed such a related art technique.

The gas sensor element is composed mainly of a solid electrolyte body 913 of oxygen ionic conductivity, a target gas electrode 914, a reference gas electrode 915, a porous diffusion resistance layer 912, and a catalyst support trap layer 92. The target gas electrode 914 and the reference gas electrode 915 are formed on both the surfaces of the solid electrolyte body 913, respectively. The target gas electrode 914 is covered with the porous diffusion resistance layer 912 through which the target gas passes. The catalyst support trap layer 92 supports a noble metal catalyst 922 (see FIG. 9) on the outer peripheral surface of the porous diffusion resistance layer 912. A part of the hydrogen gas is burned with the noble metal catalyst 922 supported in the catalyst support trap layer 92, and it is as a result possible to suppress the quick reaching of the hydrogen gas to the target gas electrode 914.

However, in view of the requirement regarding a quick response (or rapid activation) of the gas sensor element and the environmental change during a high temperature use, there is a possibility of reducing the catalyst capability of the catalyst support trap layer 92 by cohering particles of the noble metal catalyst 922 involved in the catalyst support trap layer 92 in a high temperature environment, as shown in FIG. 10B. In this case, as shown in FIG. 8A and FIG. 8B, hydrogen gas $H_2$ can pass through the porous diffusion resistance layer 912 faster than another combustion gas. As a result, the output shift from a correct output value occurs in the gas sensor element.

In addition, Japanese examined patent publication (after examination) No. JP S63-66448 has disclosed another related-art technique of the gas sensor element which has a first catalyst support trap layer and a second catalyst support trap layer where the first catalyst support trap layer is formed on the second catalyst support trap layer. Platinum (Pt), palladium (Pd), or an alloy of platinum (Pt) and palladium (Pd)

is added, as a noble metal catalyst, to the first catalyst support trap layer. Rhodium (Rh), ruthenium (Ru) or an alloy of rhodium (Rh) and ruthenium (Ru) is added, as a noble metal catalyst, to the second catalyst support trap layer. However, if the noble metal catalyst includes less palladium (Pd), there causes a possibility of cohering platinum (Pt) and rhodium (Rh) in oxidation atmosphere. On the other hand, if the noble metal catalyst includes excess amount of palladium (Pd), there is a possibility of absorbing a specified gas in the target gases by the presence of palladium (Pd). This causes deterioration of quick response capability of the gas sensor element.

SUMMARY OF THE INVENTION

It is an object of the present invention to provide an improved gas sensor element capable of preventing output shift of the gas sensor element from its correct output value, and capable of preventing deterioration of endurance of a catalyst support trap layer which forms the gas sensor element.

To achieve the above purposes, the present invention provides a gas sensor element composed mainly of a solid electrolyte body, a target gas electrode, a reference gas electrode, and a porous diffusion resistance layer. The solid electrolyte body has an oxygen ionic conductivity. The target gas electrode is formed on one surface of the solid electrolyte body, and the reference gas electrode is formed on the other surface of the solid electrolyte body. The porous diffusion resistance layer covers the target gas electrode and through which target gases to be measured are passing. The catalyst support trap layer is formed on the outer surface of the porous diffusion resistance layer and supporting noble metal catalyst. In particular, the noble metal catalyst is made of platinum, rhodium, palladium supported in the catalyst support trap layer, and an addition amount of palladium in the total amount of the noble metal catalyst is within a range of 2 to 65 wt %.

The gas sensor element according to the present invention has the catalyst support trap layer that supports the noble metal catalyst therein, and the noble metal catalyst is made of platinum (Pt), rhodium (Rh), and palladium (Pd). It is thereby possible to adequately burn hydrogen gas involved in the target gases to be measured while passing through the catalyst support trap layer. This can reduce the total amount of hydrogen gas involved in the target gases that would reach the target gas electrode, and thereby prevent the occurrence of output shift of the gas sensor element from its correct output value.

Further, because the noble metal catalyst supported in the catalyst support layer is made of rhodium (Rh) and palladium (Pd), it is possible to prevent cohesion between noble metal particles of platinum (Pt) and rhodium (Rh) to each other under oxidation atmosphere by the presence of palladium (Pd). That is, it is possible to achieve a stable state of the noble metal catalyst by adding palladium having a stable characteristic under the oxidation atmosphere into the noble metal catalyst. In addition, under the reduction atmosphere it is possible to prevent the deterioration of catalyst capability of platinum (Pt) and rhodium (Rh) of superior thermal resistance. Accordingly, it is possible to suppress the deterioration of catalyst capability of the noble metal catalyst supported in the catalyst support trap layer even if in a high temperature condition where oxidation atmosphere and reduction atmosphere are switched.

Still further, because the addition amount of palladium (Pd) is within a range of 2 to 65 wt % in the entire amount of noble metal catalyst, it is possible to adequately prevent the cohesion between platinum (Pt) metal particles and rhodium (Rh) metal particles under oxidation atmosphere and thereby possible to suppress the deterioration of catalyst capability of the noble metal catalyst.

As described above, the present invention provides the gas sensor element capable of suppressing deterioration of endurance of catalyst capability of the noble metal catalyst supported in the catalyst support trap layer while avoiding the output shift of the gas sensor element from a correct output value. In particular, when the addition amount of palladium (Pd) is less than 2 wt % in the total amount of the noble metal catalyst, there is a possibility of being difficult to suppress the cohesion between platinum (Pt) particles and rhodium (Rh) particles to each other. As a result, it becomes difficult to prevent the deterioration of endurance of catalyst capability of the noble metal catalyst.

On the contrary, when the addition amount of palladium (Pd) is more than 65 wt % in the total amount of the noble metal catalyst, excess absorption of a specified gas in the target gases occurs by the presence of excess palladium (Pd). There is as a result a possibility of being difficult to obtain the adequate response capability of the gas sensor element.

Furthermore, it is preferred to have the additional amount of palladium (Pd) within a range of 5 to 40 wt %. In this condition, it is possible to obtain a superior response capability of the gas sensor element, and to prevent the deterioration of endurance of the catalyst capability of the catalyst support trap layer.

By the way, the addition amount of palladium (Pd) of less than 5 wt % in the total amount of the noble metal catalyst causes a possibility of being difficult to suppress the occurrence of cohesion of platinum (Pt) particles and rhodium (Rh) particles to each other under oxidation atmosphere.

In addition, there is a possibility of becoming difficult to obtain the adequate response capability of the gas sensor element by occurrence of the excess absorption of a specified gas in the target gases by the presence of the excess palladium (Pd) when the addition amount of palladium (Pd) is more than 40 wt % in the total amount of the noble metal catalyst.

Still further, it is preferred to have the noble metal catalyst of not more than 5 wt % in the total amount of the catalyst support trap layer. In this condition, it is possible to prevent the occurrence of excess absorption of the target gases into the catalyst support trap layer. It is thereby possible to prevent a long-time travel of the target gases to the target gas electrode and to adequately obtain a quick response capability of the gas sensor element.

In particular, it is preferred to have not less than 0.1 wt % of the noble metal catalyst supported in the total amount of the catalyst support trap layer. In this condition, it is possible to prevent the occurrence of output shift of the gas sensor element from a correct output value.

On the contrary, when the noble metal catalyst supported is less than 0.1 wt %, there is a possibility of not decreasing an adequate amount of hydrogen gas that reaches the target gas electrode. As a result, there is a possibility of causing the difficulty of preventing the output shift of the gas sensor element from a correct output value.

Still further, it is preferred to have a thickness of 10 to 300 μm of the catalyst support trap layer. This can avoid the occurrence of causing output shift of the gas sensor element form a correct output value while maintaining the quick response capability of the gas sensor element.

On the contrary, when the thickness of the catalyst support trap layer is less than 10 μm, it becomes difficult to adequately absorb hydrogen gas in the catalyst support trap layer. This thereby causes the output shift of the gas sensor element form a correct output value.

When the thickness of the catalyst support trap layer is more than 300 μm, because it takes a long time for the target gases to reach the target gas electrode, it becomes impossible to obtain the gas sensor element with a quick response. Further, there is a possibility of easily separating the catalyst support trap layer from the outer surface of the porous diffusion resistance layer.

Furthermore, it is preferred for the gas sensor element to have a width of a range of 3.0 to 5.0 mm and a thickness of a range of 1.0 to 2.5 mm. This condition of the gas sensor element according to the present invention can provide the improved features such as action and feature described above. Because such a small sized gas sensor element has a small thermal capacity, a thermal resistance capability of the catalyst in the catalyst support trap layer becomes an important matter. However, the gas sensor element to which the present invention is applied can prevent the deterioration of endurance of the catalyst capability and have an adequate strength with a quick activation capability of the catalyst.

On the other hand, when the gas sensor element has a width of less than 3.0 mm, it becomes difficult to provide the gas sensor element having an adequate strength.

Furthermore, when the gas sensor element has a width of more than 5.0 mm, because the gas sensor element has a large thermal capacity, it becomes impossible to provide the gas sensor element with a rapid activation capability.

It is preferred that the gas sensor element is an air-fuel (A/F) sensor element capable of detecting an Air-fuel ratio by measuring a critical current that depends on the oxygen concentration involved in the target gases.

Such an A/F sensor element has a long diffusion length measured from the outer surface of the porous diffusion resistance layer to the target gas electrode through which the target gases are passing. This increases a difference of reaching time length to the target gas electrode between oxygen gas and hydrogen gas, and thereby causes the occurrence of the output shift of the gas sensor element from its correct output value. Accordingly, the gas sensor element of the present invention can provide the superior action and effects described above.

BRIEF DESCRIPTION OF THE DRAWINGS

A preferred, non-limiting embodiment of the present invention will be described by way of example with reference to the accompanying drawings, in which.

DETAILED DESCRIPTION OF THE PREFERRED EMBODIMENTS

Figure 1:
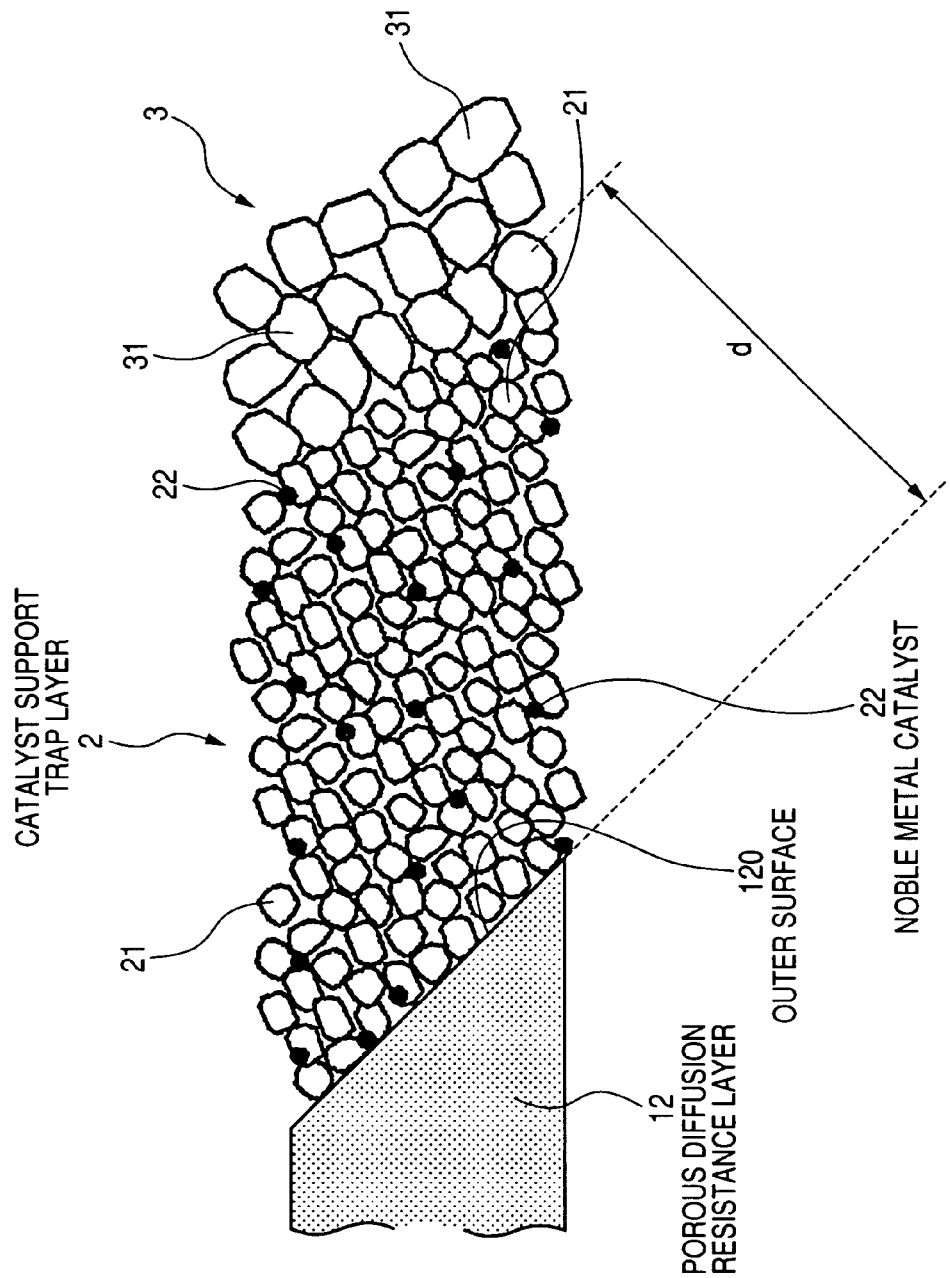
FIG. 1 is a view mainly showing a catalyst support trap layer formed on a porous diffusion resistance layer in a gas sensor element according to an embodiment of the present invention.

Hereinafter, various embodiments of the present invention will be described with reference to the accompanying drawings. In the following description of the various embodiments, like reference characters or numerals designate like or equivalent component parts throughout the several diagrams.

Embodiment

A description will be given of the gas sensor element of a preferred embodiment according to the present invention with reference to FIG. 1 to FIG. 7A, and FIG. 7B.

As shown in FIG. 1, FIG. 3, FIGS. 7A and 7B, the gas sensor element 1 of the preferred embodiment of the present invention has a solid electrolyte body 13 of an oxygen ionic conductivity, a target gas electrode 14, a reference gas electrode 15, a porous diffusion resistance layer 12, and a catalyst support trap layer 2. The target gas electrode 14 is formed on one surface of the solid electrolyte body 13, and the reference gas electrode 15 is formed on the other surface of the solid electrolyte body 13. The target gas electrode 14 is covered with the porous diffusion resistance layer 12 through which the target gas passes. The catalyst support trap layer 2 supports a noble metal catalyst 22 formed on the outer peripheral surface 120 of the porous diffusion resistance layer 12.

The noble metal catalyst 22 supported in the catalyst support trap layer 2 is composed of platinum (Pt), rhodium (Rh), and palladium (Pd).

The noble metal catalyst 22 supported is within a range of 0.1% to 5.0% in the total weight of the catalyst support trap layer 2. An addition amount of palladium is within a range of 5.0 to 40.0% in the total amount of the noble metal catalyst 22.

Next, a description will be given of the gas sensor element according to the preferred embodiment in detail.

The gas sensor element 1 of the preferred embodiment has a built-in air-fuel (A/F) sensor capable of detecting an air-fuel (A/F) ratio by measuring the amount of a critical current which depends on the concentration of oxygen involved in target gases.

Figure 3:
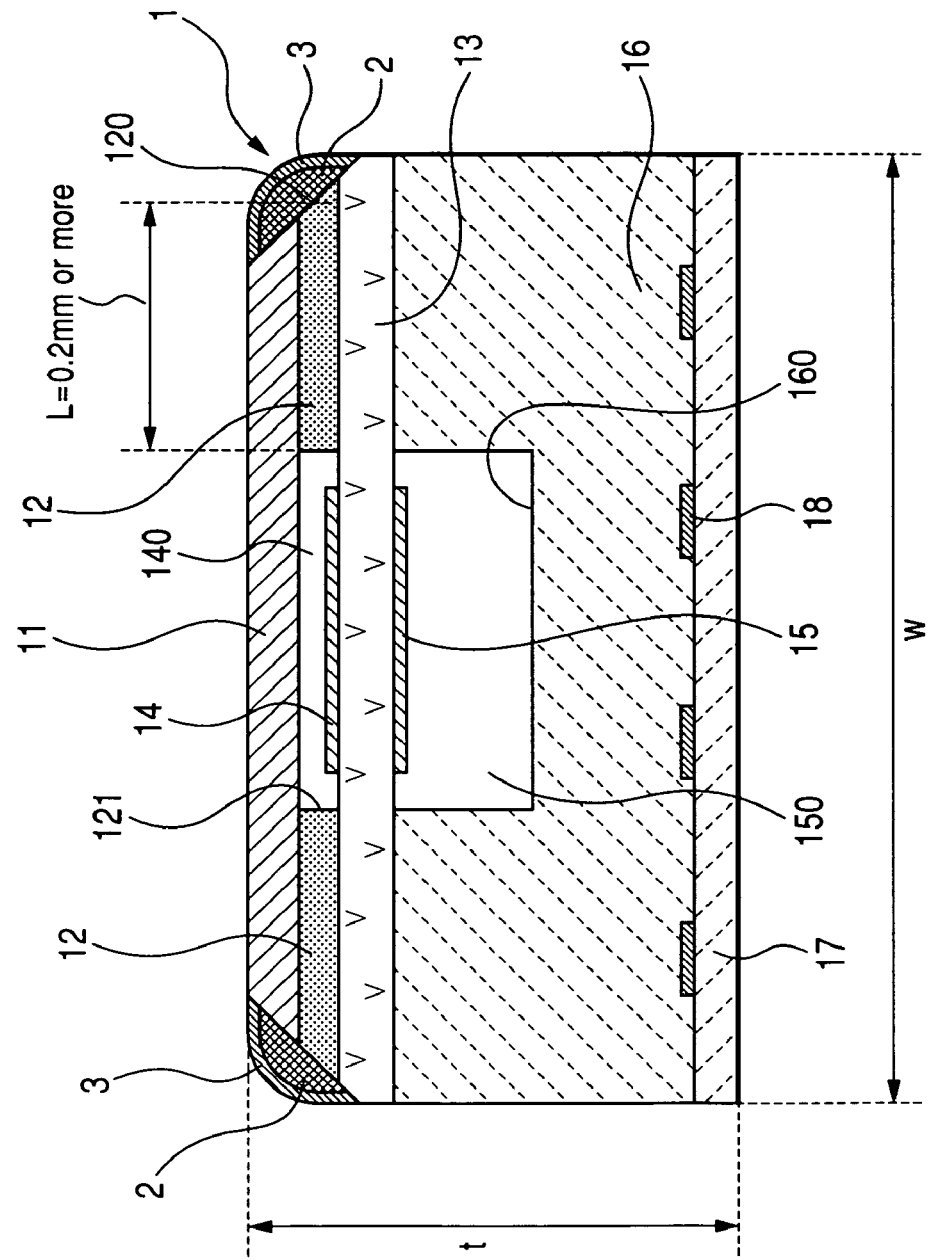
FIG. 3 is a sectional view of the gas sensor element in a direction perpendicular to a longitudinal axis of the gas sensor element of the embodiment shown in FIG. 1.

As shown in FIG. 3, the gas sensor element 1 of the embodiment has a width of a range of 3.0 mm to 5.0 mm and a thickness of a range of 1.0 mm to 2.5 mm. The gas sensor element 1 has a built-in the target gas electrode 14 made of platinum formed on the surface of the solid electrolyte body 13 of the oxygen ion conductivity made of zirconia. The reference electrode 15 is formed on the opposed surface of the solid electrolyte body 13.

As shown in FIG. 3, the solid electrolyte body 13 is laminated on a reference gas formation layer 16 of an electric insulation made of alumina ceramics as a dense substance capable of preventing any passage of gas.

A groove 160 is formed in the reference gas formation layer 16 made of alumina. This groove 160 acts as a reference gas room 150 into which air or atmosphere is introduced and filled as a reference gas.

As shown in FIG. 3, the reference gas formation layer 16 is laminated on a heater substrate 17 that is equipped with some heating bodies 18 faced to the reference gas formation layer 16. The heating bodies 18 are heated by electricity. Further, as shown in FIG. 3, a dense shielding layer 11 is faced to the target gas electrode 14 and made of alumina capable of preventing any passage of gas. The dense shielding layer 11 is laminated on the porous diffusion resistance layer 12.

The porous diffusion resistance layer 12 has an opening 121 and formed between the shielding layer 11 and the solid electrolyte body 13. The target gas measuring room 140 is surrounded by the shielding layer 11, the porous diffusion resistance layer 12, and the solid electrolyte body 13.

Figure 2:
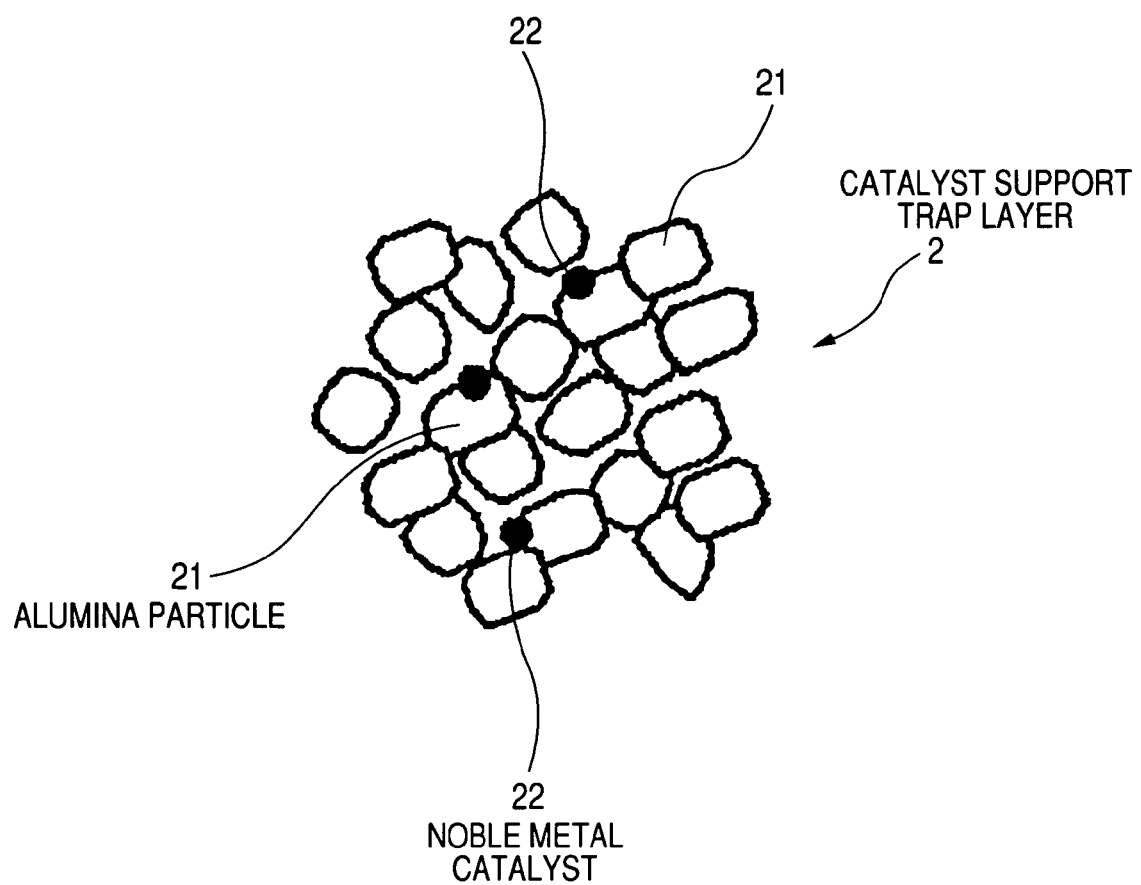
FIG. 2 is a view showing components forming the catalyst support trap layer in the gas sensor element of the embodiment shown in FIG. 1.
Figure 4:
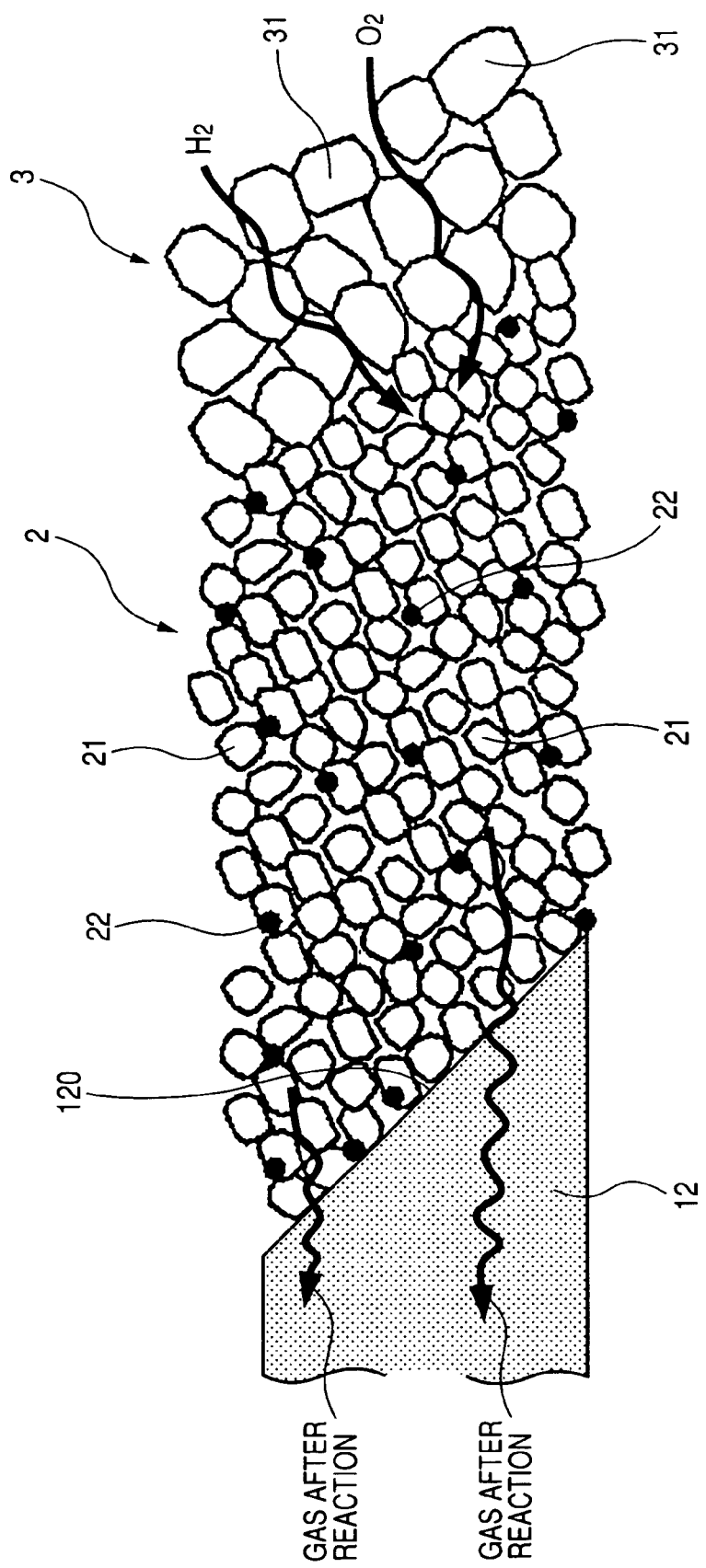
FIG. 4 is a sectional view showing an introduction path of target gases in the gas sensor element of the embodiment shown in FIG. 1.

As described above, the catalyst support trap layer 2 supporting the catalyst noble metal 22 shown in FIG. 1 to FIG. 4 is formed on the outer surface of the porous diffusion resistance layer 12. The catalyst support trap layer 2 in the gas sensor element 1 of the embodiment is made of plural alumina particles 21 having a crystal structure of γ or θ type, as shown in FIG. 1, FIG. 2, and FIG. 4.

The alumina particle has an average diameter of a range of 1 to 50 μm. The catalyst support trap layer 2 has an average porosity (or void content) of a range of 40 to 70%, and an average diameter of porosity of a range of 0.1 to 10 μm.

As shown in FIG. 1 and FIG. 3, the catalyst support trap layer 2 has an average thickness "d" of a range of 10 to 300 μm formed on the outer surface of the porous diffusion resistance layer 12. As shown in FIG. 3, the diffusion distance "L" in the porous diffusion resistance layer 12 is not less than 0.2 mm, which is the line measured from the outer surface 120 of the porous diffusion resistance layer 12 to the target gas electrode 14. Through the preferred embodiment, the diffusion distance "L" is measured from the outer peripheral surface 120 to the opening part 121 of the porous diffusion resistance layer 12.

As shown in FIG. 1, FIG. 3, and FIG. 4, a protection trap layer 3 is made of alumina particles 31 and formed on the outer surface of the catalyst support trap layer 2 in the gas sensor element 1. Each alumina particle 31 in the protection trap layer 3 has an average diameter of a range of 10 μm to 50 μm, an average porosity of a range of 40 to 70%, and an average diameter of porosity of a range of 1 to 10 μm. Although the protection trap layer 3 does not support any noble metal catalyst, it is acceptable to support it so as to enhance the endurance or durability of the protection trap layer 3. The formation of both the catalyst support trap layer 2 and the protection trap layer 3 can prevent the deterioration of the porous diffusion resistance layer 12 and the target gas electrode 14 from the adhesion of poisonous materials such as P (phosphorus), Ca (calcium), Pb (lead or plumbum).

The protection trap layer 3 covering the catalyst support trap layer 2 can prevent scattering of noble metal particles involved in the noble metal catalyst 22.

A description will now be given of the path to the target gas electrode 14 through which the target gases are passing. In the preferred embodiment, the target gases to be measured are hydrogen gas ($H_2$) and oxygen gas ($O_2$).

As shown in FIG. 4, hydrogen gas and oxygen gas involved in the target gases reach the catalyst support trap layer 2 after passing through the protection trap layer 3. Because the noble metal catalyst 22 made of platinum (Pt), rhodium (Rh), and palladium (Pd) is supported in the catalyst support trap layer 2, hydrogen gas and oxygen gas are reacted to each other by the noble metal catalyst 22 and the chemical reaction generates water.

Most of hydrogen gas is burned in the catalyst support trap layer 2, and as a result this burning of hydrogen gas can prevent the introduction of a large volume of water in the target gas electrode 140.

As shown in FIG. 3 and FIG. 4, after passing through the catalyst support trap layer 2, the oxygen gas reaches the target gas electrode 14 through the porous diffusion resistance layer 12.

Next, a description will now be given of action and effects of the gas sensor element of the embodiment according to the present invention.

As shown in FIG. 1, FIG. 2, and FIG. 4, the gas sensor element 1 has the catalyst support trap layer 2 that supports the noble metal catalyst 22. The catalyst support trap layer 2 is made of platinum (Pt), rhodium (Rh), and palladium (Pd). While the target gases move through the catalyst support trap layer 2, most of hydrogen gases involved in the target gases is burned adequately. As a result, the amount of hydrogen gas involved in the target gases which reach the target gas electrode 14 is adequately decreased. This can prevent the output shift of the gas sensor element 1 from a correct output value caused by the presence of hydrogen gas.

Further, because the noble metal catalyst 22 supported by the catalyst support trap layer 2 is made of platinum (Pt), rhodium (Rh), and palladium (Pd), it is possible to prevent the cohesion of the noble metal catalyst particles such as platinum (Pt) and rhodium (Rh) to each other under the oxidation atmosphere. That is, it is possible to promote the stability of the noble metal catalyst 22 under the oxidation atmosphere by adding palladium (Pd) having a stable characteristic in oxidation atmosphere.

It is possible to prevent the deterioration of catalyst function of the noble metal catalyst by the presence of platinum (Pt) and rhodium (Rh) having a superior heat resistance under the reducing atmosphere (or reduction atmosphere). Accordingly, it is possible to suppress the durability of the catalyst capability in the catalyst support trap layer 2 under a high temperature environment where oxidation atmosphere and reducing atmosphere (or reduction atmosphere) are changed.

An addition amount of palladium (Pd) into the entire noble metal catalyst 22 is within a range of 5 to 40 wt %. This further prevents the deterioration of the catalyst capability by adequately suppressing cohesion between platinum (Pt) and rhodium (Rh) under the oxidation atmosphere. It is further possible to provide the superior gas sensor element 1 having a quick response while preventing excess absorption of a specified gas involved in the target gases by the presence of palladium (Pd).

Still further, because the noble metal catalyst 22 supports the specified gas of only 5 wt % or less in the entire weight of the catalyst support trap layer 2, it can prevent the excess absorption of the target gas in the catalyst support trap layer 2, and because this can prevent the extension of time to reach the target gases to the target electrode 14, it is possible to provide the gas sensor element with a quick response characteristic.

Still further, because the noble metal catalyst 22 has a supporting weight of not less than 0.1 wt % to the entire weight of the catalyst support trap layer 2, it is possible to prevent the output shift of the gas sensor element from its correct output value.

Furthermore, as shown in FIG. 1, because the catalyst support trap layer 2, has an average thickness "d" of a range of 10 to 300 μm, it is possible to keep the response characteristic of the gas sensor element 1 while suppressing the generation of the output shift from its correct output value.

Figure 7A:
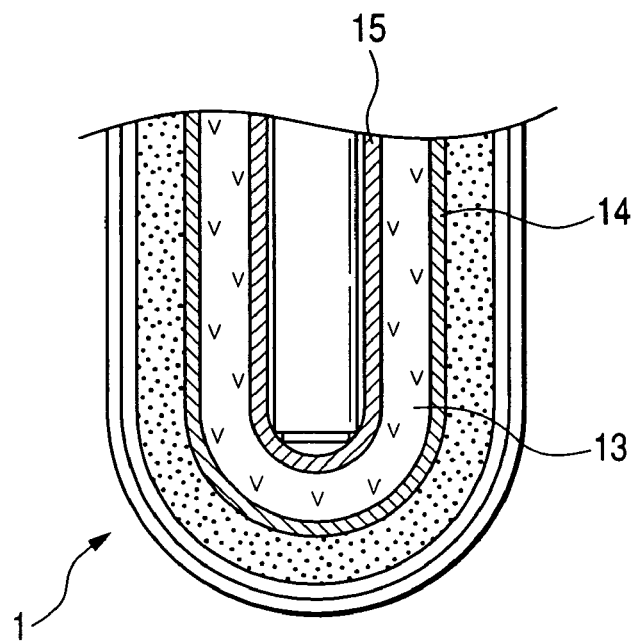
FIG. 7A is a partially sectional view showing the gas sensor element according to the embodiment shown in FIG. 3.
Figure 7B:
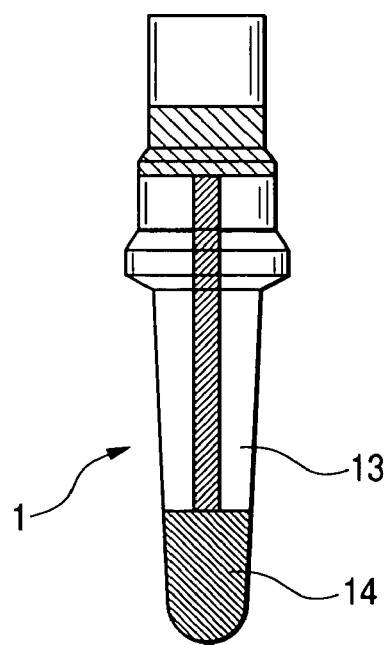
FIG. 7B is a perspective view showing the gas sensor element according to the embodiment shown in FIG. 3.
Figure 8A:
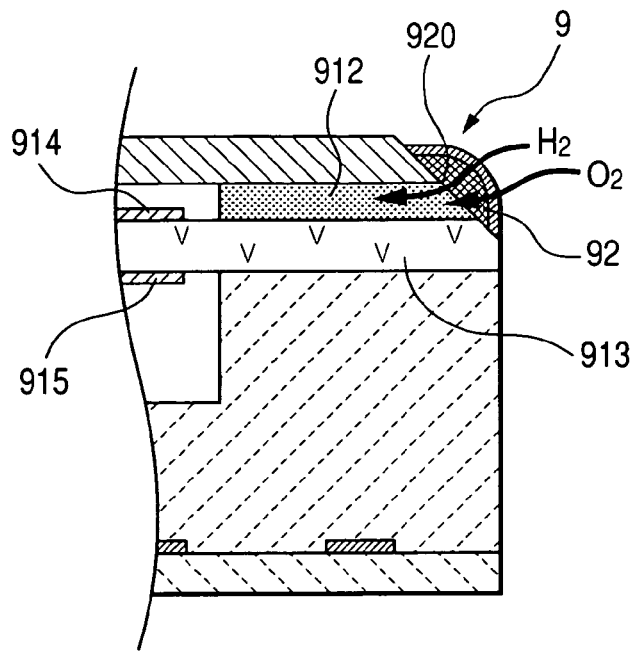
FIG. 8A is a sectional view of a catalyst support trap layer in a gas sensor element as a related-art through which target gases to be measured are passing.
Figure 8B:
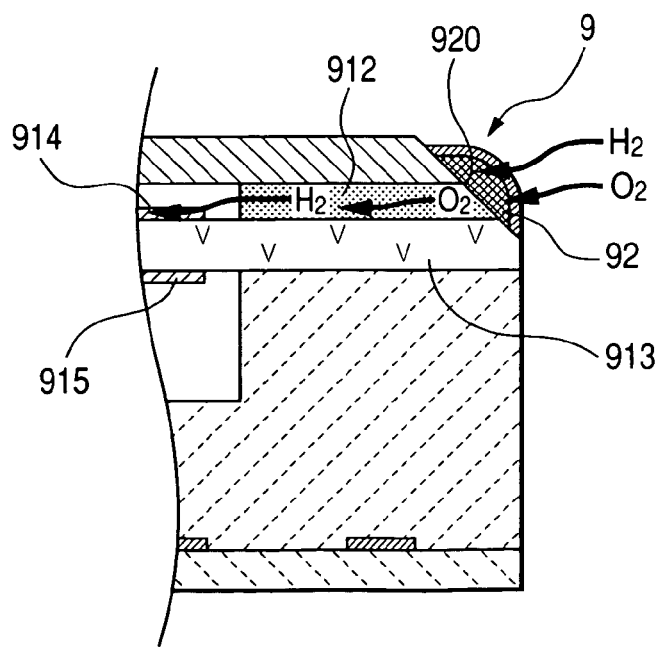
FIG. 8B is a sectional view of the catalyst support trap layer in the related-art gas sensor element, which shows a state of reaching the target gases to the target gas electrode in a measurement room.
Figure 9:
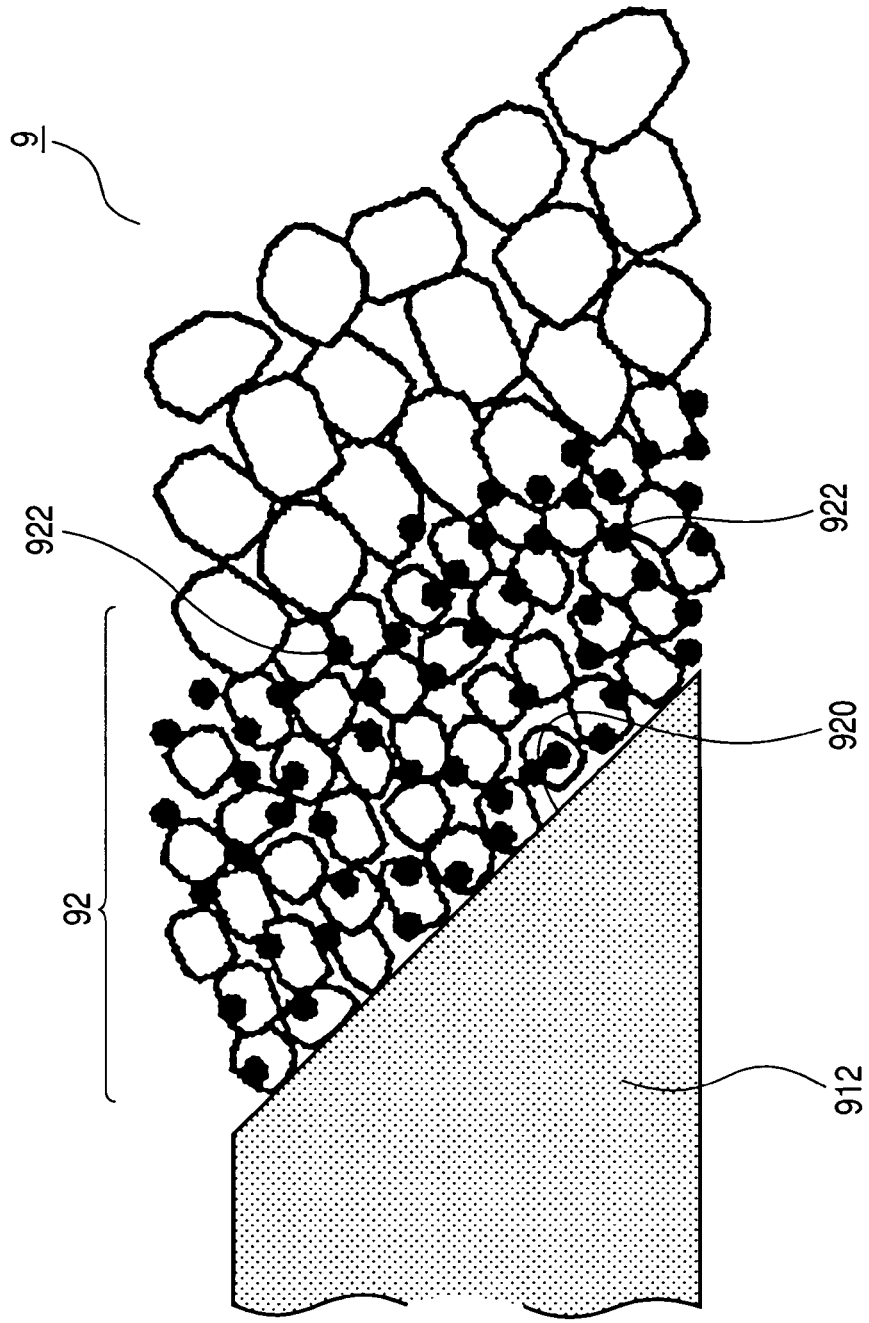
FIG. 9 is a sectional view showing a detailed catalyst support trap layer that is formed on an outer peripheral surface of a porous diffusion resistance layer in the gas sensor element as the related-art.
Figure 10A:
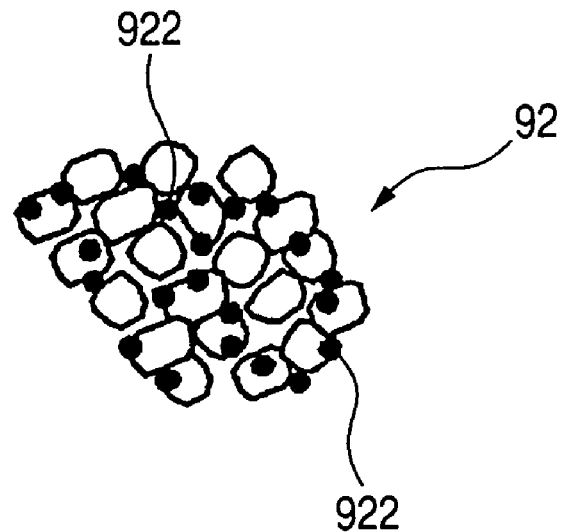
FIG. 10A shows components that form the catalyst support trap layer in the gas sensor element according to the related-art before breaking its endurance capability (or durability)
Figure 10B:
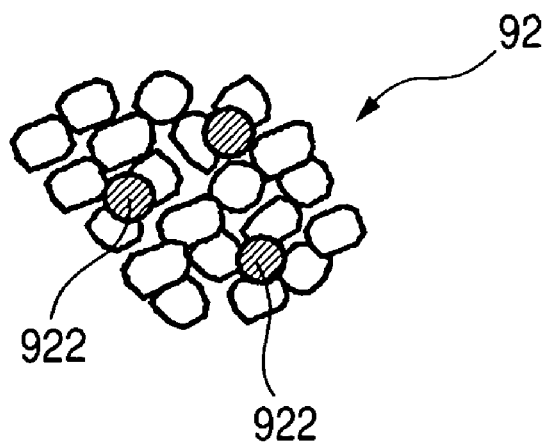
FIG. 10B shows the components that form the catalyst support trap layer in the gas sensor element according to the related-art after breaking its endurance capability (or durability).

As shown in FIG. 3, FIG. 7A, and FIG. 7B, because the gas sensor element 1 of the preferred embodiment has a width of a range of 3.0 mm to 5.0 mm and a thickness "t" of a range of 1.0 mm to 2.5 mm, it is possible to provide the gas sensor element having an adequate strength with a rapid response capability while maintaining the superior action and effects described above according to the present invention.

The gas sensor element 1 of the present invention is applied to an air-fuel (A/F) sensor element capable of detecting an air-fuel ratio by measuring a critical current depending on the concentration of oxygen gas involved in the target gases. Such an A/F sensor element has a long diffusion length L in the porous diffusion resistance layer 12, which is the length from the outer surface 120 of the porous diffusion resistance layer 12 to the target gas electrode 14. The increase of the diffusion length L increases a difference in time of reaching the target gas electrode 14 between oxygen gas and hydrogen gas, and as a result there is a possibility of causing the output shift of the gas sensor element from its correct output value. On the contrary, the gas sensor element 1 having the configuration described above according to the present invention can provide a correct output value without any shifting from the correct output value.

As described above, according to the present invention, it is possible to prevent the occurrence of output shift from a correct output value of the gas sensor element, and further to provide the gas sensor element capable of suppressing deterioration of the catalyst capability of the catalyst support trap layer 2.

First Experiment

A description will now be given of the first experiment of the gas sensor element of the embodiment with reference to FIG. 5.

Figure 5:
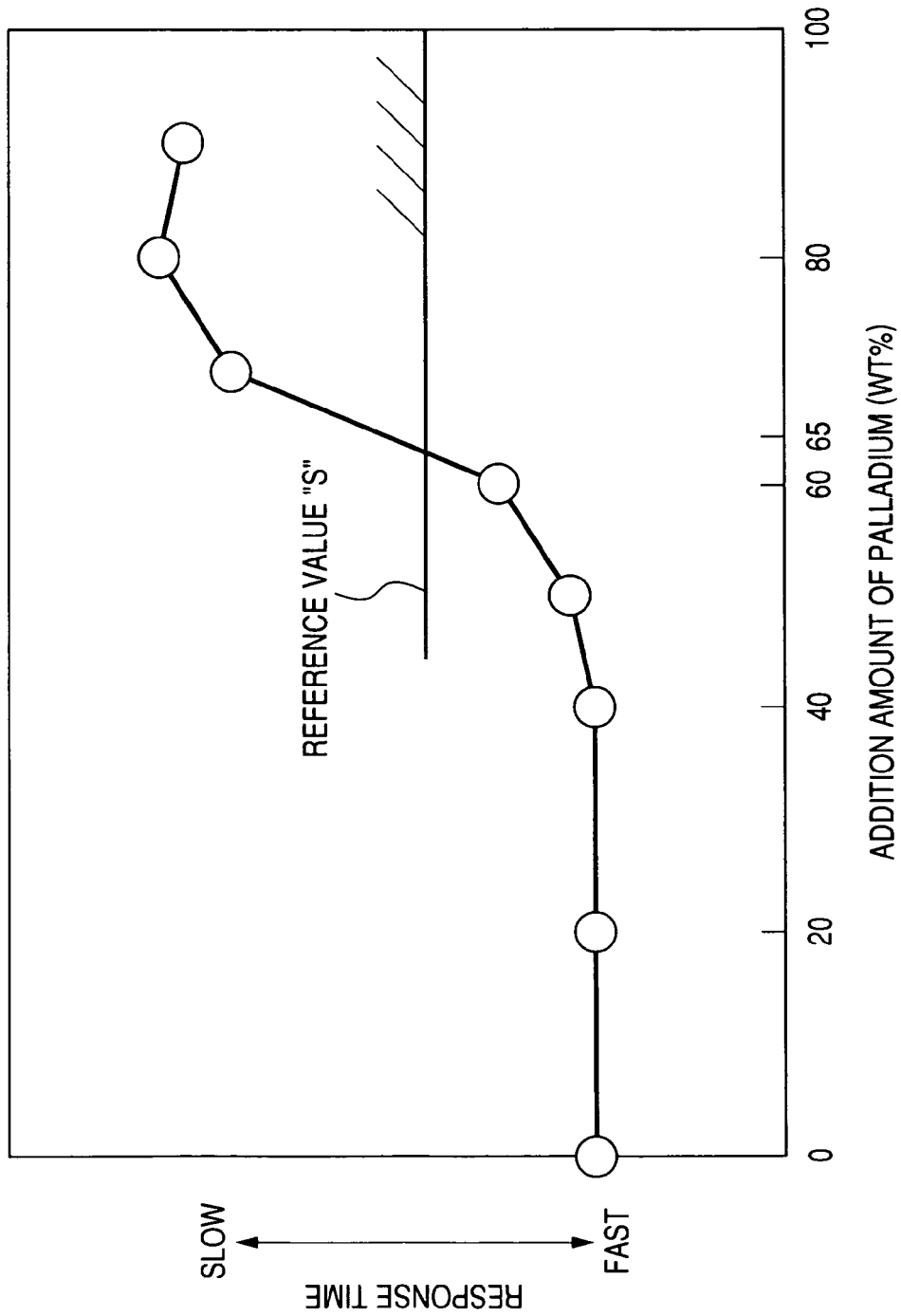
FIG. 5 shows the measurement results of a first experiment indicating the relationship between the addition amount of palladium (Pd) in the entire amount of the noble metal catalyst supported by the catalyst support trap layer and a response time of the gas sensor element.

FIG. 5 shows the measurement results of the first experiment which indicate the relationship between the addition amount of palladium into the noble metal catalyst 22 supported in the catalyst support trap layer 2 and the response time of the gas sensor element 1.

The amount of the noble metal catalyst 22 has 1 wt % in the weight of the entire catalyst support trap layer 2. In FIG. 5, the vertical line indicates the response time of the gas sensor element 1 and the horizontal line indicates the addition amount of palladium (Pd).

As clearly shown in FIG. 5, it is possible to have the response time of the gas sensor element below the reference value "S" when the additional amount of palladium (Pd) is set to not more than 65 wt %.

On the contrary, when the addition amount of palladium (Pd) is more than 65 wt %, the response time becomes over the reference value "S". This means that the response capability of the gas sensor element becomes reduced.

Accordingly, the first experimental results shown in FIG. 5 clearly indicate that it is necessary to have not more than 65 wt % of the additional amount of palladium (Pd) in the noble metal catalyst 22.

Second Experiment

A description will now be given of the second experiment of the gas sensor element of the embodiment with reference to Table 1 and FIG. 6.

The second experiment shows the relationship between the time of endurance of the gas sensor element and the stoichiometric shift (or output shift) Δλ before and after breaking of the endurance of the gas sensor element while changing the additional amount of palladium (Pd) to the entire noble metal catalyst.

The amount of the noble metal catalyst 22 has 1 wt % in the weight of the entire catalyst support trap layer 2. In FIG. 6, the vertical line indicates the stoichiometric shift Δλ of the gas sensor element 1 and the horizontal line indicates the time of endurance.

In the embodiment, the stoichiometric shift Δλ means the shift value of a concrete air-fuel ratio (A/F ratio) from its theoretical A/F ratio. A large amount of the stoichiometric shift Δλ indicates that the gas sensor element 1 does not perform correctly, namely the catalyst support trap layer 2 does not operate correctly.

Table 1 shows the addition amount of palladium (Pd) in each of the samples E1 to E7 of the gas sensor element.

TABLE 1

| Sample No. | Addition amount of Pd (wt %) |
|---|---|
| Sample E1 | 1 |
| Sample E2 | 5 |
| Sample E3 | 10 |
| Sample E4 | 20 |
| Sample E5 | 30 |
| Sample E6 | 50 |
| Sample E7 | 90 |

In the above endurance test (or life test), each of the samples E1 to E7 was inserted in a gas sensor, and the gas sensor element incorporated in each gas sensor was continuously heated at 900° C. by using available city-gas combustion/ventilation apparatus.

Figure 6:
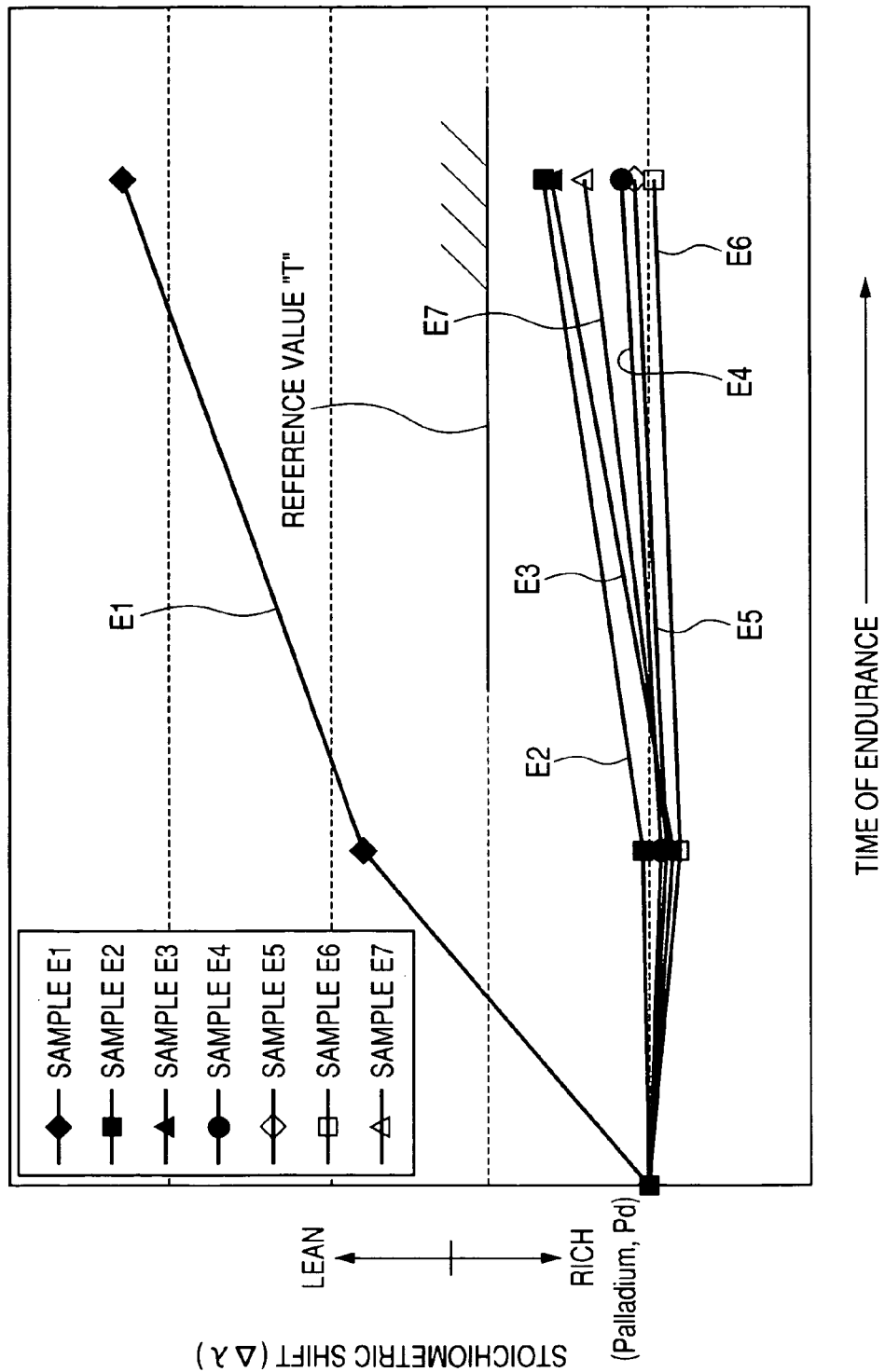
FIG. 6 shows the measurement results of a second experiment indicating the relationship between the time of endurance and the stoichiometric shift (as output shift) of the gas sensor element.

FIG. 6 shows the measurement results of the second experiment indicating the relationship between the time of endurance and the stoichiometric shift of Samples E1 to E7 of the gas sensor element.

As clearly shown in FIG. 6, the samples E2 to E7 having the rich additional amount of palladium (Pd) of not less than 5 wt % have low stoichiometric shift Δλ that is less than the reference value "T". Thus, the gas sensor element having the additional amount of palladium (Pd) of not less than 5 wt % can decrease the stoichiometric shift Δλ as low as possible.

On the contrary, the sample E1 of the gas sensor element having the lean additional amount of palladium (Pd) of 1 wt % (less than 5 wt %) has the high stoichiometric shift Δλ than the reference value "T" according to the increase of the time of endurance.

As described above, it is preferred for the gas sensor element to have the additional amount of palladium (Pd) of more than at least 1 wt %.

While specific embodiments of the present invention have been described in detail, it will be appreciated by those skilled in the art that various modifications and alternatives to those details could be developed in light of the overall teachings of the disclosure. Accordingly, the particular arrangements disclosed are meant to be illustrative only and not limited to the scope of the present invention which is to be given the full breadth of the following claims and all equivalent thereof.

What is claimed is:

1. A gas sensor element to be used in a direct injection gasoline engine or compresses natural gas engine, comprising:
   a solid electrolyte body of oxygen ionic conductivity;
   a target gas electrode formed on one surface of the solid electrolyte body;
   a reference gas electrode formed on the other surface of the solid electrolyte body;
   a porous diffusion resistance layer covering the target gas electrode and through which target gas comprising oxygen gas and hydrogen gas as a detection target moves to the target gas electrode;
   a catalyst support trap layer compound of alumina particles and noble metal catalyst formed on the outer surface of the porous diffusion resistance layer and supporting the noble metal catalyst so that the hydrogen gas contained in the target gas is trapped by the noble metal catalyst and burned in the catalyst support trap layer in order to suppress the hydrogen gas from reaching the target gas electrode; and
   a protection trap layer made of alumina particles formed on the outer surface of the catalyst support trap layer,
   wherein the noble metal catalyst is made of platinum, rhodium, and palladium which are supported in the catalyst support trap layer, and an amount of said palladium in a total amount of the noble metal catalyst made of platinum, rhodium and palladium is within a range of 20 to 50 wt %,
   the content of the noble metal catalyst is within a range of not less than 0.1 wt % to not more than 5 wt % of the entire content of the catalyst support trap layer,
   the gas sensor element is an air to fuel sensor element capable of detecting an air to fuel ratio by measuring a critical current depending on oxygen concentration in the target gas,
   a traveling length of the target gas passing through the porous diffusion resistance layer covering the target gas electrode is not less than 0.2 mm, and
   the alumina particles contained in the catalyst support trap layer have an average diameter within a range of 1 to 50 μm, an average porosity in the catalyst support trap layer is within a range of 40 to 70%, and an average diameter of each porosity is within a range of 0.1 to 10 μm, and
   the alumina particles contained in the protection trap layer have an average diameter within a range of 10 to 50 μm, an average porosity in the protection trap layer is within a range of 40 to 70%, and an average diameter of each porosity is within a range of 1 to 10 μm.

2. The gas sensor element according to claim 1, wherein the catalyst support trap layer has a thickness within a range of 10 to 300 μm.

3. The gas sensor element according to claim 1, wherein the gas sensor element has a width of a range of 3.0 to 5.0 mm and a thickness of a range of 1.0 to 2.5 mm.

* * * * *

UNITED STATES PATENT AND TRADEMARK OFFICE
CERTIFICATE OF CORRECTION

PATENT NO.        : 7,867,370 B2
APPLICATION NO.   : 11/633434
DATED             : January 11, 2011
INVENTOR(S)       : Tsuji et al.

It is certified that error appears in the above-identified patent and that said Letters Patent is hereby corrected as shown below:

Title Page;
In the Assignee Field of the issued patent, please replace:
"DENSO CORPORATION, KARIYA CITY, AICHI-PREF., JAPAN"

WITH

--DENSO CORPORATION, KARIYA CITY, AICHI-PREF., JAPAN
  NIPPON SOKEN, INC., NISHIO CITY, AICHI-PREF., JAPAN--

Signed and Sealed this
Eighth Day of February, 2011

David J. Kappos
*Director of the United States Patent and Trademark Office*